United States Patent
Tokida et al.

(10) Patent No.: US 11,497,466 B2
(45) Date of Patent: Nov. 15, 2022

(54) DIAGNOSTIC IMAGING CATHETER

(71) Applicant: TERUMO KABUSHIKI KAISHA, Tokyo (JP)

(72) Inventors: Masanori Tokida, Fujinomiya (JP); Takuya Uno, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 387 days.

(21) Appl. No.: 16/728,622

(22) Filed: Dec. 27, 2019

(65) Prior Publication Data

US 2020/0129149 A1 Apr. 30, 2020

Related U.S. Application Data (63) Continuation of application No. PCT/JP2018/024705, filed on Jun. 28, 2018.

(30) Foreign Application Priority Data

Jun. 29, 2017 (JP) .............................. JP2017-127635

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/4461* (2013.01); *A61B 8/5207* (2013.01); *A61B 90/36* (2016.02);
(Continued)

(58) Field of Classification Search
CPC ...... A61B 2090/3784; A61B 2562/227; A61B 2562/228; A61B 5/0066; A61B 5/0084;
(Continued)

(56) References Cited

U.S. PATENT DOCUMENTS

| | | | |
|---|---|---|---|
| 2011/0048764 A1* | 3/2011 | Hira | H01B 11/10 174/105 R |
| 2013/0223798 A1* | 8/2013 | Jenner | G02B 6/3604 385/77 |
| 2018/0199916 A1 | 7/2018 | Sugihara et al. | |

FOREIGN PATENT DOCUMENTS

| | | |
|---|---|---|
| JP | H08102344 A | 4/1996 |
| JP | 2006048998 A | 2/2006 |
| | (Continued) | |

OTHER PUBLICATIONS

An English Translation of the International Search Report (Form PCT/ISA/210) and the Written Opinion of the International Searching Authority (Form PCT/ISA/237) dated Aug. 14, 2018, by the Japanese Patent Office in corresponding International Application No. PCT/JP2018/024705. (7 pages).

(Continued)

*Primary Examiner* — Michael T Rozanski
(74) *Attorney, Agent, or Firm* — Buchanan, Ingersoll & Rooney PC (57) ABSTRACT

A diagnostic imaging catheter is disclosed, which is capable of preventing a solution from an internal space of a hub from flowing into a portion communicating with the internal space of the hub and to which the signal lines such as the optical fiber and the electric signal cable are electrically or optically connected. The optical diagnostic catheter includes a rotatable drive shaft, an elongated sheath configured to be inserted into a biological lumen, a hub that includes a port connected to the sheath for supplying the solution, a connector portion that includes an optical connector accommodated in an internal space of the hub and optically connected to an external optical connector, a first seal portion that prevents the solution from the port from flowing into a first connection portion, and a second seal portion that prevents (Continued)

the solution from the port from flowing into a second connection portion.

20 Claims, 8 Drawing Sheets (51) Int. Cl.
*A61B 8/08* (2006.01)
*A61B 90/00* (2016.01)
*A61M 25/00* (2006.01)

(52) U.S. Cl.
CPC .... *A61M 25/0014* (2013.01); *A61M 25/0097* (2013.01); *A61B 2090/3784* (2016.02)

(58) Field of Classification Search
CPC ....... A61B 5/6852; A61B 5/6876; A61B 8/12; A61B 8/445; A61B 8/4461; A61B 8/5207; A61B 8/56; A61B 90/36; A61M 25/0014; A61M 25/0097; H01R 13/2442; H01R 2107/00; H01R 2201/12; H01R 24/86
See application file for complete search history.

(56) References Cited

FOREIGN PATENT DOCUMENTS

| JP | 2013542041 A | 11/2013 |
|----|--------------|---------|
| WO | 2015/107833 A1 | 7/2015 |
| WO | 2015141136 A1 | 9/2015 |
| WO | 2017/047330 A1 | 3/2017 |

OTHER PUBLICATIONS

International Search Report (PCT/ISA/210) and translation and Written Opinion (PCT/ISA/237) dated Aug. 14, 2018, by the Japanese Patent Office as the International Searching Authority for International Application No. PCT/JP2018/024705.

The extended European Search Report dated Feb. 16, 2021, by the European Patent Office in corresponding European Patent Application No. 18823483.5-1126. (6 pages).

* cited by examiner

DIAGNOSTIC IMAGING CATHETER

CROSS-REFERENCES TO RELATED APPLICATIONS

This application is a continuation of International Application No. PCT/JP2018/024705 filed on Jun. 28, 2018, which claims priority to Japanese Application No. 2017-127635 filed on Jun. 29, 2017, the entire content of both of which is incorporated herein by reference.

FIELD OF THE DISCLOSURE

The present disclosure generally relates to an image diagnosis catheter.

BACKGROUND DISCUSSION

Diagnostic imaging catheters used to acquire a diagnostic image for diagnosing a diseased site in a living body include a diagnostic imaging catheter that acquires images by an intra vascular ultra sound (IVUS) diagnosis method and an optical coherence tomography (OCT) diagnosis method, or an optical frequency domain imaging (OFDI) method is used.

The diagnostic imaging catheter acquires a tomographic image by irradiating an ultrasound or light while rotating about a longitudinal direction of the catheter as a rotation axis, receiving a reflected wave, and processing a signal. For example, among the above catheters, in a diagnostic imaging catheter using IVUS, a hub is provided at a proximal portion of the catheter. The hub is provided with a cleaning port used when a solution such as a cleaning solution is flowed to a distal end of the catheter through an internal space of the hub (refer to JP-T-2013-542041 below). A motor driving device (also referred to as motor driving unit: MDU) for rotating a component that emits the ultrasound on the distal end of the catheter is disposed on the proximal end from the hub.

In the diagnostic imaging catheter, there are so-called a dual-type catheter which acquires a tomographic image with each of an ultrasound and light, in addition to the above-described types using the ultrasound such as IVUS and the types using light such as OCT and OFDI.

In the case of a dual-type diagnostic imaging catheter, a signal line such as an optical fiber or an electric signal cable is disposed inside the catheter. The signal line is inserted into the internal space of the hub on the proximal end, and is electrically or optically connected to a component related to image formation at a connection point with the MDU. In the vicinity of the connection point with the MDU in the vicinity of the hub, the signal line, for example, the optical fiber and the electric signal cable can be electrically or optically connected to the above components, and a solution, for example, a priming solution can flow through in the internal space of the hub from a port. Therefore, a structure for preventing the solution such as the priming solution from flowing through a portion where electrical or optical connection is performed is necessary.

SUMMARY

A diagnostic imaging catheter is disclosed that communicates with an internal space of a hub and can help prevent a solution from flowing through the internal space of the hub at a portion where a signal line, for example, an optical fiber and an electric signal cable is electrically or optically connected.

An diagnostic imaging catheter according to the present disclosure can include a rotatable drive shaft in which an optical transmitter and receiver and an ultrasound transmitter and receiver are disposed on a distal portion, and an optical fiber connected to the optical transmitter and receiver and a signal line connected to the ultrasound transmitter and receiver are disposed, an elongated sheath configured to be inserted into a biological lumen, into which the drive shaft can be inserted, and the elongated sheath including a lumen through which a solution flows, a hub that includes a port supplying the solution to the lumen of the sheath, and an internal space communicating with the lumen of the sheath, through which the solution from the port flows and the optical fiber and the signal line are inserted, a connector portion that includes an optical connector accommodated in the internal space of the hub and optically connected to an external optical connector provided in an external device and the optical fiber, and an electrical connector electrically connected to an external electrical connector provided in the external device and the signal line, a first seal portion that prevents the solution from the port from flowing into a first connection portion between the optical connector and the optical fiber, and a second seal portion that helps prevents the solution from the port from flowing into a second connection portion between the signal line and the electrical connector.

The diagnostic imaging catheter according to the present disclosure includes the first seal portion sealing that the solution from the port flows into the first connection portion between the optical connector and the optical fiber, and the second seal portion sealing that the solution from the port flows into the second connection portion between the signal line and the electrical connector. Therefore, the solution from the internal space can be prevented from flowing into a portion to which the signal lines such as the optical fiber and the electric signal cable are electrically or optically connected.

In accordance with an aspect, a diagnostic imaging catheter is disclosed comprising: a rotatable drive shaft having an optical transmitter and receiver and an ultrasound transmitter and receiver disposed on a distal portion of the rotatable drive shaft, and an optical fiber connected to the optical transmitter and receiver and a signal line connected to the ultrasound transmitter and receiver; an elongated sheath configured to be inserted into a biological lumen, the drive shaft configured to be inserted into the elongated sheath, and the elongated sheath including a lumen through which a solution flows; a hub that includes a port supplying the solution to the lumen of the sheath, and an internal space communicating with the lumen of the sheath, the lumen configured to receive the solution from the port and wherein the optical fiber and the signal line are inserted into the lumen; a connector portion that includes an optical connector accommodated in the internal space of the hub and optically connected to an external optical connector provided in an external device and the optical fiber, and an electrical connector electrically connected to an external electrical connector provided in the external device and the signal line; a first seal portion configured to prevent the solution from the port from flowing into a first connection portion between the optical connector and the optical fiber; and a second seal portion configured to prevent the solution from the port from flowing into a second connection portion between the signal line and the electrical connector.

In accordance with another aspect, a connector is disclosed for a diagnostic imaging catheter, the connector comprising: a connector portion that includes an optical connector accommodated in the internal space of a hub configured to supply a solution to a lumen of an elongated sheath, the lumen being optically connected to an external optical connector provided in an external device and an optical fiber connected to an optical transmitter and receiver, and an electrical connector electrically connected to an external electrical connector provided in the external device and a signal line connected to an ultrasound transmitter and receiver; a first seal portion configured to prevent the solution from the port from flowing into a first connection portion between the optical connector and the optical fiber; and a second seal portion configured to prevent the solution from the port from flowing into a second connection portion between the signal line and the electrical connector.

In accordance with an aspect, a method is disclosed for using a diagnostic imaging catheter, the method comprising: injecting a solution into a lumen of an elongated sheath of the diagnostic imaging catheter through a connector portion that includes an optical connector accommodated in the internal space of a hub configured to supply the solution to the lumen of an elongated sheath and optically connected to an external optical connector provided in an external device and an optical fiber connected to an optical transmitter and receiver and, and an electrical connector electrically connected to an external electrical connector provided in the external device and a signal line connected to an ultrasound transmitter and receiver; preventing the solution from the port from flowing into a first connection portion between the optical connector and the optical fiber with a first seal portion; and preventing the solution from the port from flowing into a second connection portion between the signal line and the electrical connector with a second seal portion.

BRIEF DESCRIPTION OF THE DRAWINGS

FIGS. 2A and 2B are diagrams schematically illustrating an overall configuration of the diagnostic imaging catheter according to the embodiment, and wherein

DETAILED DESCRIPTION

Set forth below with reference to the accompanying drawings is a detailed description of embodiments of a diagnostic imaging catheter representing examples of the inventive diagnostic imaging catheter. The dimensions or scales on the drawings may be exaggerated or different from actuality/reality for convenience of description and illustration. The following description does not limit the technical scope and terms used in the aspects.

Figure 1:
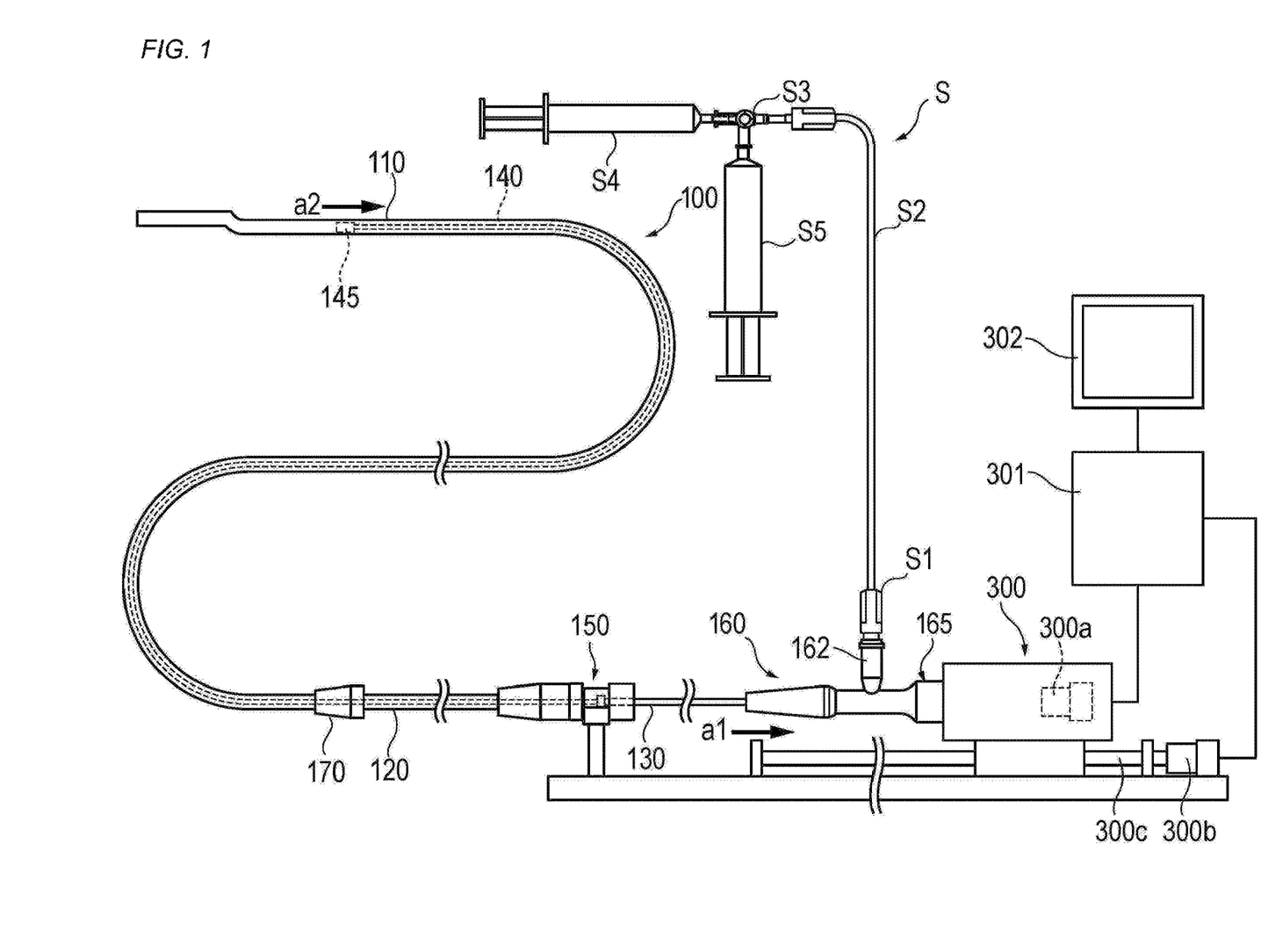
FIG. 1 is a plan view illustrating a state where an external device is connected to a diagnostic imaging catheter according to an embodiment of the present disclosure.
Figure 2A:
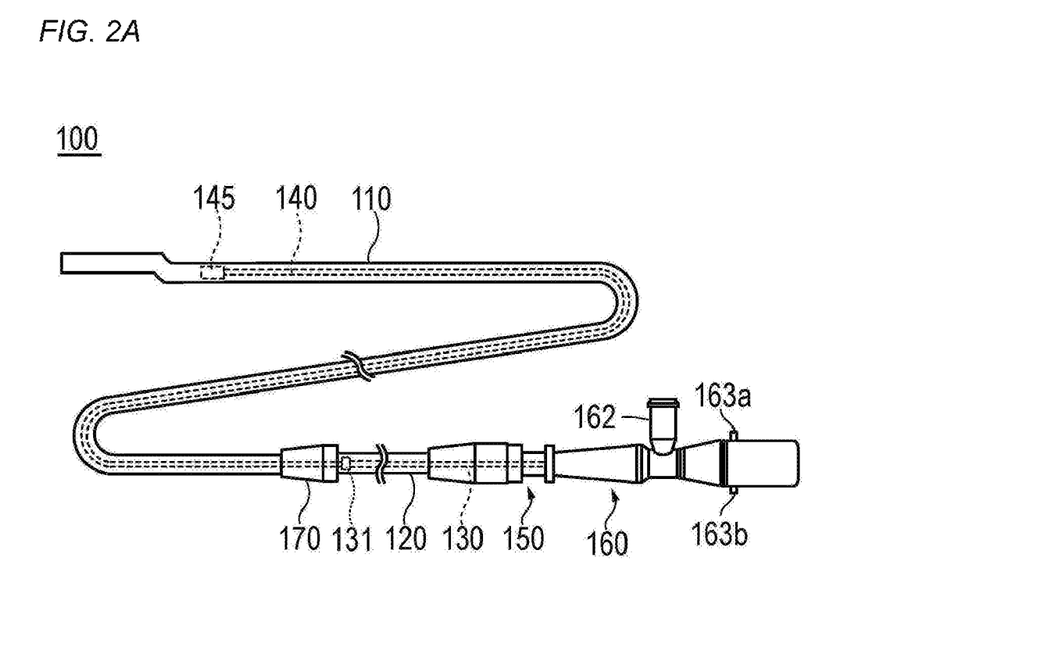
FIG. 2A is a side view of the diagnostic imaging catheter before performing a pull-back operation (thinning operation)
Figure 2B:
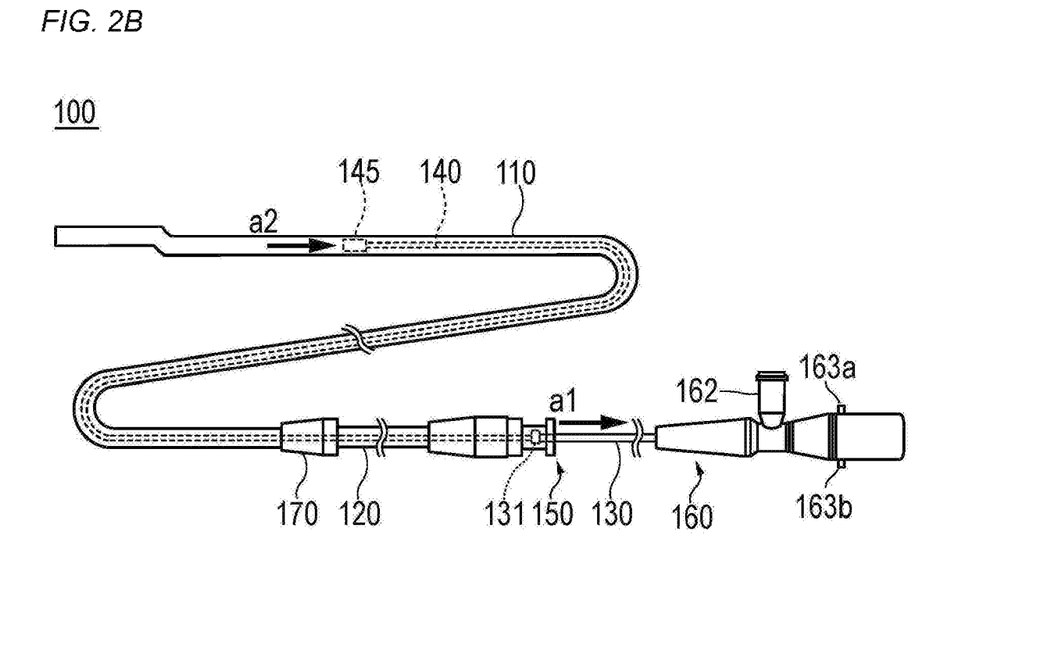
FIG. 2B is a side view of the diagnostic imaging catheter when the pull-back operation is performed.
Figure 3:
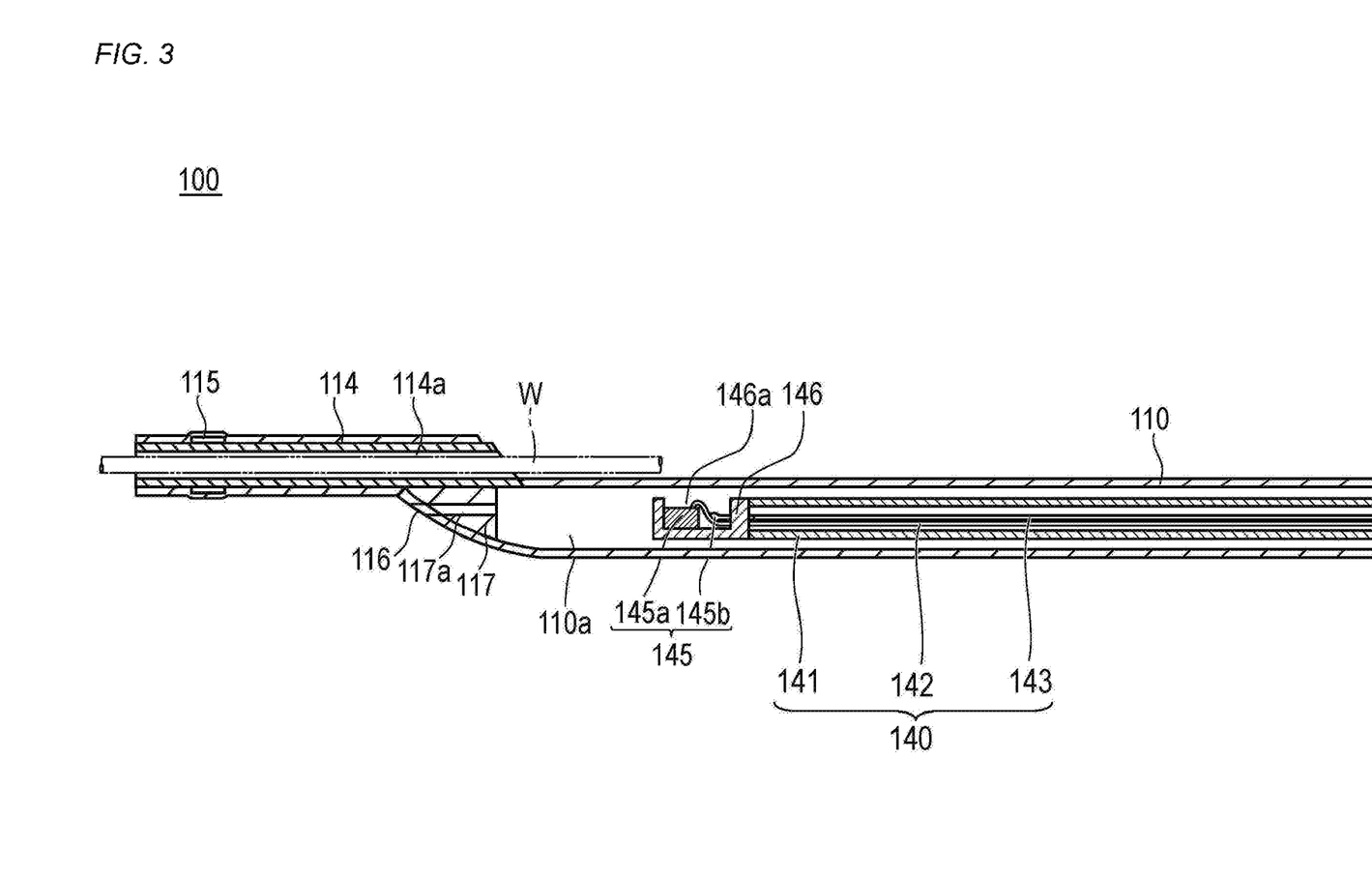
FIG. 3 is an enlarged cross-sectional view illustrating a configuration of a distal end of the diagnostic imaging catheter according to the embodiment.
Figure 4:
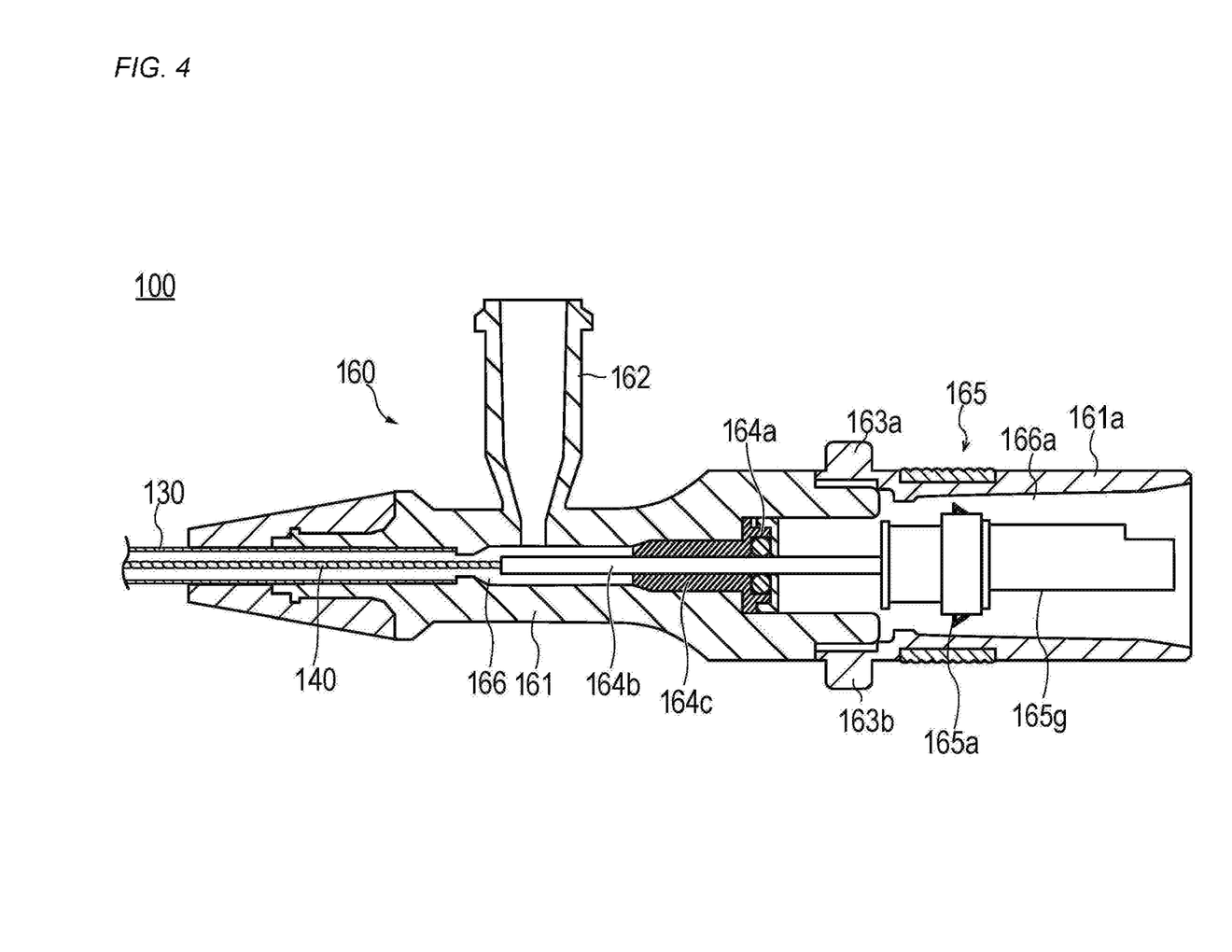
FIG. 4 is an enlarged cross-sectional view illustrating a configuration of a proximal end of the diagnostic imaging catheter according to the embodiment.

FIG. 1 is a plan view illustrating a state where an external device 300 is connected to a diagnostic imaging catheter 100 according to the present embodiment. FIGS. 2A and 2B are diagrams schematically illustrating an overall configuration of the diagnostic imaging catheter 100 according to the embodiment. FIG. 3 is a diagram illustrating a configuration of a distal end of the diagnostic imaging catheter 100 according to the embodiment. FIG. 4 is a diagram illustrating a configuration of a proximal end of the diagnostic imaging catheter 100 according to the embodiment. FIGS. 5 to 9 are diagrams for describing a connector portion accommodated in a connector case illustrated in FIG. 4.

In accordance with an exemplary embodiment, the diagnostic imaging catheter 100 according to the present embodiment is a dual-type diagnostic imaging catheter having both functions of an intra vascular ultra sound (IVUS) diagnosis method and an optical coherence tomography (OCT) diagnosis method. As illustrated in FIG. 1, the diagnostic imaging catheter 100 is driven by being connected to the external device 300.

The diagnostic imaging catheter 100 will be described with reference to FIGS. 1 to 4.

As illustrated in FIGS. 1, 2A, and 2B, the diagnostic imaging catheter 100 includes a sheath 110 to be inserted into a body-cavity of a living body, an outer tube 120 provided on a proximal end of the sheath 110, an inner shaft 130 inserted into the outer tube 120 so as to be movable forward (distal direction) and backward (proximal direction), a drive shaft 140 rotatably provided in the sheath 110 having a signal transmitter and receiver 145 transmitting and receiving signals at a distal end, a unit connector 150 provided on the proximal end of the outer tube 120 and configured to receive the inner shaft 130, and a hub 160 provided on the proximal end of the inner shaft 130.

In the description of the specification, a side inserted into the body-cavity of the diagnostic imaging catheter 100 is referred to as a distal end or a distal end side. A hub 160 side provided in the diagnostic imaging catheter 100 is referred to as a proximal end or a proximal end side. An extending direction of the sheath 110 is referred to as an axial direction.

As illustrated in FIG. 2A, the drive shaft 140 extends to the inside of the hub 160 through the sheath 110, the outer tube 120 is connected to the proximal end of the sheath 110, and the inner shaft 130 is inserted into the outer tube 120.

The hub 160, the inner shaft 130, the drive shaft 140, and the signal transmitter and receiver 145 are connected to each other so as to move forward (i.e., distal direction) and backward (i.e., proximal direction) integrally (i.e., together) in the axial direction. Therefore, for example, when the hub 160 is pushed toward the distal end side, the inner shaft 130 connected to the hub 160 is pushed (i.e., moved in the distal direction) into the outer tube 120 and the unit connector 150, and the drive shaft 140 and the signal transmitter and receiver 145 moves inside the sheath 110 toward the distal end side. For example, when the operation of pulling (i.e., moved in the proximal direction) the hub 160 toward the proximal end side is performed, the inner shaft 130 is pulled out from the outer tube 120 and the unit connector 150 as illustrated by an arrow a1 in FIGS. 1 and 2B. The drive shaft 140 and the signal transmitter and receiver 145 move inside the sheath 110 toward the proximal end side as indicated by an arrow a2.

As illustrated in FIG. 2A, when the inner shaft 130 is pushed to the distal end side, a distal portion of the inner shaft 130 reaches the vicinity of a relay connector 170. At this time, the signal transmitter and receiver 145 is located in the vicinity of the distal end of the sheath 110. The relay connector 170 is a connector that connects the sheath 110 and the outer tube 120.

As illustrated in FIG. 2B, a connector 131 for preventing disconnection is provided at the distal end of the inner shaft 130. The connector 131 for preventing disconnection has a function of preventing the inner shaft 130 from coming out of the outer tube 120. When the hub 160 is pulled toward the proximal end side, that is, when the inner shaft 130 is pulled from the outer tube 120 and the unit connector 150, the connector 131 for preventing disconnection is configured to be caught at a predetermined position on an inner wall of the unit connector 150.

As illustrated in FIG. 3, the drive shaft 140 is provided with a flexible tubular body 141, and an electric signal cable 142 (corresponding to "signal line") and an optical fiber 143 connected to the signal transmitter and receiver 145 are disposed in the flexible tubular body 141 of the drive shaft 140. The tubular body 141 can be, for example, a multilayer coil having different winding directions around the axis. Examples of the material constituting the multilayer coil of the tubular body 141 can include stainless steel and Ni—Ti (nickel and titanium) alloy. In the present embodiment, the electric signal cable 142 is provided with two signal lines 142a and 142b that are electrically connected to electrode terminals 165b provided in a connector portion 165 described later, and extend like parallel lines (refer to FIG. 9).

The signal transmitter and receiver 145 includes the ultrasound transmitter and receiver 145a that transmits and receives the ultrasound and the optical transmitter and receiver 145b that transmits and receives light.

The ultrasound transmitter and receiver 145a is provided with a transducer, and has a function of transmitting the ultrasound based on a pulse signal into the body-cavity and receiving the ultrasound reflected from a biological tissue in the body-cavity. The ultrasound transmitter and receiver 145a is electrically connected to the electrode terminal 165b (refer to FIG. 4) via the electric signal cable 142.

As the transducer provided in the ultrasound transmitter and receiver 145a, for example, a piezoelectric material such as ceramics or quartz can be used.

The optical transmitter and receiver 145b continuously transmits a transmitted measurement light into the body-cavity and continuously receives a reflected light from the biological tissue in the body-cavity. The optical transmitter and receiver 145b is provided at the distal end of the optical fiber 143, and has a ball lens (optical element) having a lens function for condensing light and a reflection function for reflecting light.

The signal transmitter and receiver 145 is accommodated in a housing 146. The proximal end of the housing 146 is connected to the drive shaft 140. The housing 146 has a shape in which an opening portion 146a is provided on a cylindrical surface of a cylindrical metal pipe so as not to hinder the progress of the ultrasound transmitted and received by the ultrasound transmitter and receiver 145a and light transmitted and received by the optical transmitter and receiver 145b. The housing 146 can be formed, for example, by laser processing, and can also be formed by cutting from metal mass, or metallic powder injection molding (MIM).

As illustrated in FIG. 3, the sheath 110 is provided with a lumen 110a into which the drive shaft 140 is inserted so as to be movable forward and backward. A guide wire insertion member 114 provided with a guide wire lumen 114a that is parallel to the lumen 110a provided in the sheath 110 and into which a second guide wire W to be described later can be inserted is attached to the distal portion of the sheath 110. The sheath 110 and the guide wire insertion member 114 can be integrally formed, for example, by heat-welding or the like. The guide wire insertion member 114 can be provided, for example, with a marker 115 having X-ray contrast properties. The marker 115 can be formed of a metal pipe having high radiopacity such as platinum (Pt) and gold (Au). Note that, for the purpose of improving the mechanical strength, an alloy in which iridium (Ir) is mixed with platinum (Pt) aforementioned may be used. Furthermore, the marker 115 may be formed of a metal coil instead of a metal pipe.

A communication hole 116 that communicates the inside of the lumen 110a with the outside of the lumen 110a is formed at the distal portion of the sheath 110. In addition, a reinforcing member 117 for firmly joining and supporting the guide wire insertion member 114 is provided at the distal portion of the sheath 110. The reinforcing member 117 is formed with a communication passage 117a that communicates the inside of the lumen 110a disposed on the proximal end from the reinforcing member 117 and the communication hole 116. Note that the reinforcing member 117 may not be provided at the distal portion of the sheath 110.

In accordance with an exemplary embodiment, the communication hole 116 is a priming solution discharge hole for discharging a priming solution. When the diagnostic imaging catheter 100 is used in a mode for acquiring a tomographic image by IVUS, priming processing of filling the sheath 110 with the priming solution is performed. For example, in a case where ultrasound is transmitted without filling the sheath 110 with the priming solution, due to a large difference in acoustic impedance between a matching layer disposed on the surface of the transducer of the ultrasound transmitter and receiver 145a and the air, the ultrasound is reflected at the interface between the matching layer and the air, and there is a possibility that the ultrasound cannot reach a wall of the biological lumen deeply. On the other hand, by filling the sheath 110 with the priming solution, since the priming solution has an acoustic impedance value close to that of the matching layer, the ultrasound can reach the wall of the biological lumen rather deeply. When performing the priming processing, the priming solution can be discharged to the outside from the communication hole 116 and the gas, for example, air can be discharged from the inside of the sheath 110 together with the priming solution.

The distal portion of the sheath 110, which is the range in which the signal transmitter and receiver 145 moves in the axial direction of the sheath 110, includes a window portion that is formed to have higher permeability of inspection waves such as light and an ultrasound than other portions.

In accordance with an exemplary embodiment, the sheath 110, the guide wire insertion member 114, and the reinforcing member 117 are formed of a flexible material, the material is not particularly limited, and examples of the materials of the sheath 110, the guide wire insertion member 114, and the reinforcing member 117 can include various thermoplastic elastomers such as styrene-based, polyolefin-based, polyurethane-based, polyester-based, polyimide-based, polyimide-based, polybutadiene-based, trans polyisoprene-based, fluorine rubber-based, and chlorinated polyethylene-based. One or a combination of two or more of these materials (polymer alloy, polymer blend, laminate, and the like) can also be used. Note that a hydrophilic lubricating coating layer that exhibits lubricity when wet can be disposed on the outer surface of the sheath 110.

As illustrated in FIG. 4, the hub 160 includes a hub main body 161 having a hollow shape, a connector case 161a connected to the proximal end of the hub main body 161, a port 162 communicating with the lumen 110a of the sheath 110 and supplying a solution to the lumen 110a, projections 163a and 163b for determining the position (direction) of the hub 160 when connecting to the external device 300, a connection pipe 164b holding the drive shaft 140, a bearing 164c rotatably supporting the connection pipe 164b, a sealing member 164a preventing the priming solution from leaking from between the connection pipe 164b and the bearing 164c toward the proximal end side, and the connector portion 165 in which the electrode terminal 165b and an optical connector 165a connected to the external device 300 are disposed.

As illustrated in FIG. 4, the hub main body 161 is provided with an internal space 166 that communicates with the lumen 110a of the sheath 110 and through which the solution from the port 162 flows. The proximal end of the inner shaft 130 is accommodated in the internal space 166 of the hub main body 161, and the electric signal cable 142 and optical fiber 143 of the drive shaft 140 are inserted through the inner shaft 130. In addition, the internal space 166 houses the connection pipe 164b and the bearing 164c. The drive shaft 140 is pulled out from the inner shaft 130 in the internal space 166 of the hub main body 161.

As illustrated in FIG. 4, the connector case 161a is a component provided at the proximal end of the hub 160 and connected to the hub main body 161. The connector case 161a is provided with an internal space 166a accommodating the connector portion 165. In accordance with an exemplary embodiment, the internal space 166a houses a portion of the MDU components serving as a power source required for rotation of the drive shaft 140 and movement along the rotation axis. In the present specification, the internal space 166 of the hub main body 161 and the internal space 166a of the connector case 161a corresponds to the internal space of the hub 160.

In accordance with an exemplary embodiment, the port 162 is connected to an injection device S (refer to FIG. 1) for injecting a priming solution when performing the priming processing. The injection device S is provided with a connector S1 connected to the port 162, a tube S2 connected to the connector S1, a three-way stopcock S3 connected to the tube S2, and a first syringe S4 and a second syringe S5 which are connected to the three-way stopcock S3 and can inject the priming solution into the port 162. In accordance with an exemplary embodiment, the second syringe S5 has a larger capacity than that of the first syringe S4, and can be a syringe that is used as an auxiliary in a case where the amount of the priming solution injected by the first syringe S4 is insufficient.

The connection pipe 164b holds the drive shaft 140 in order to transmit the rotation of the electrode terminal 165b and the optical connector 165a which are rotationally driven by the external device 300 to the drive shaft 140. The electric signal cable 142 and the optical fiber 143 (refer to FIG. 3) are inserted into the connection pipe 164b.

Referring again to FIG. 1, the diagnostic imaging catheter 100 is connected to the external device 300 and driven rotationally and axially.

As aforementioned, the external device 300 is connected to the connector portion 165 provided on the proximal end of the hub 160 (refer to FIG. 4). Details of the connector portion 165 will be described later.

In addition, the external device 300 includes a motor 300a that is a power source for rotating the drive shaft 140, and a motor 300b that is a power source for moving the drive shaft 140 in the axial direction. The rotational motion of the motor 300b is converted into axial motion by a direct motion conversion mechanism 300c connected to the motor 300b. As the direct motion conversion mechanism 300c, for example, a ball screw, a rack and pinion mechanism, or the like can be used.

The operation of the external device 300 is controlled by a control apparatus 301 electrically connected to the external device 300. The control apparatus 301 includes a central processing unit (CPU) and a memory as main components. The control apparatus 301 is electrically connected to a monitor 302.

Next, the connector portion 165 will be described with reference to FIGS. 4 to 9.

Figure 6:
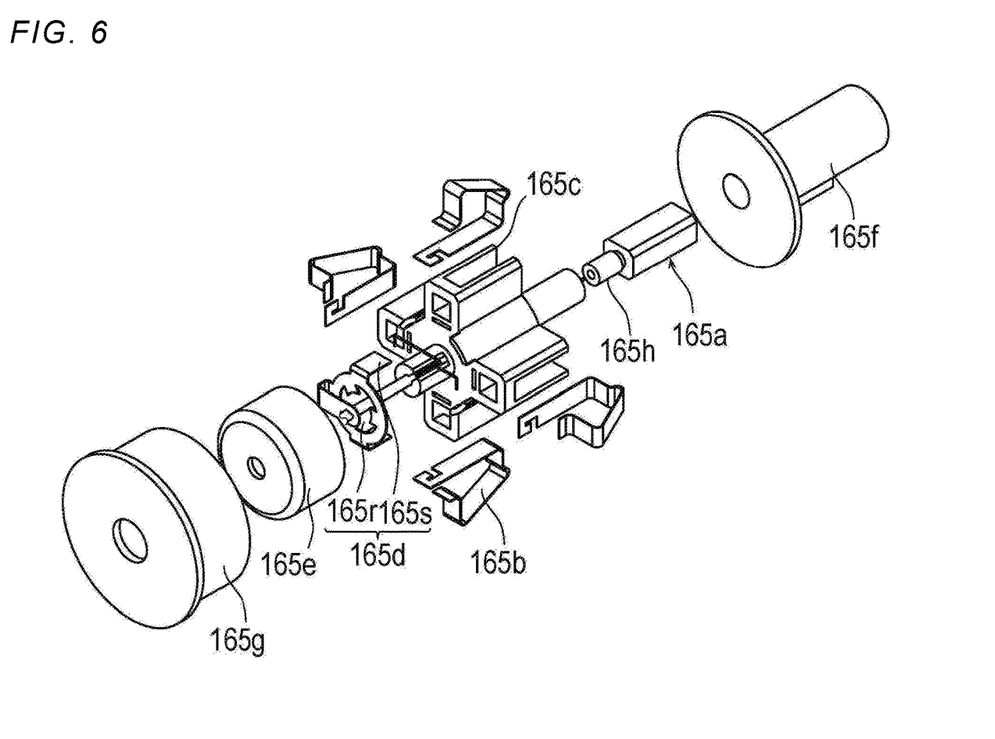
FIG. 6 is an exploded perspective view of the connector portion as illustrated in FIG. 5.
Figure 7:
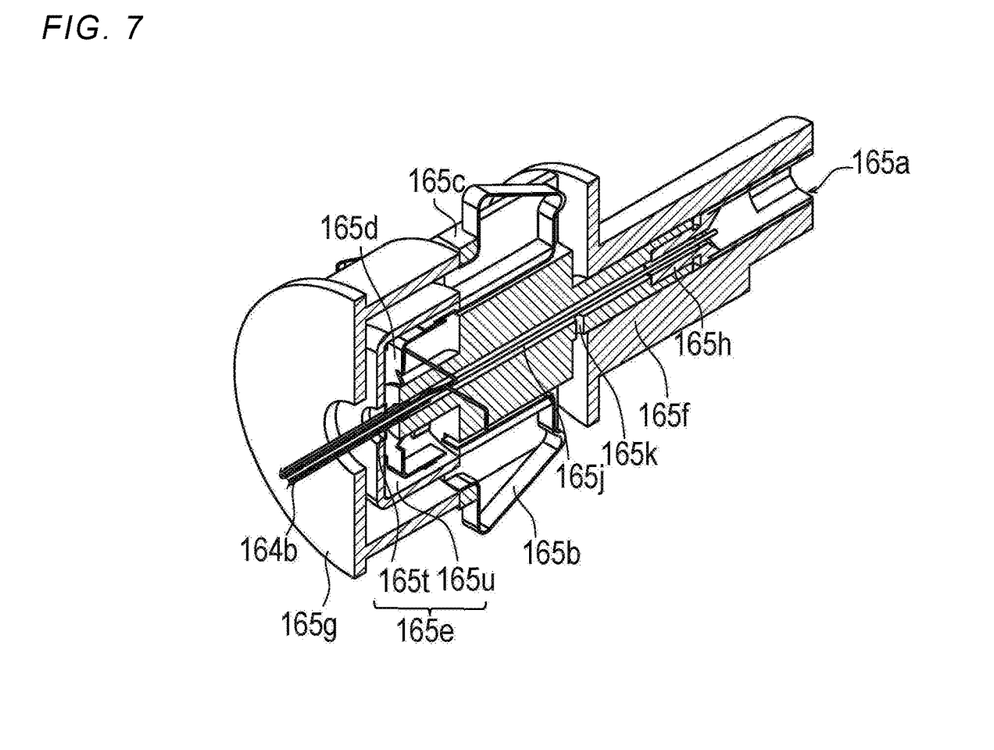
FIG. 7 is a perspective view illustrating a state where a component group in FIG. 5 is cut at a position passing through a central axis (rotation axis).
Figure 8:
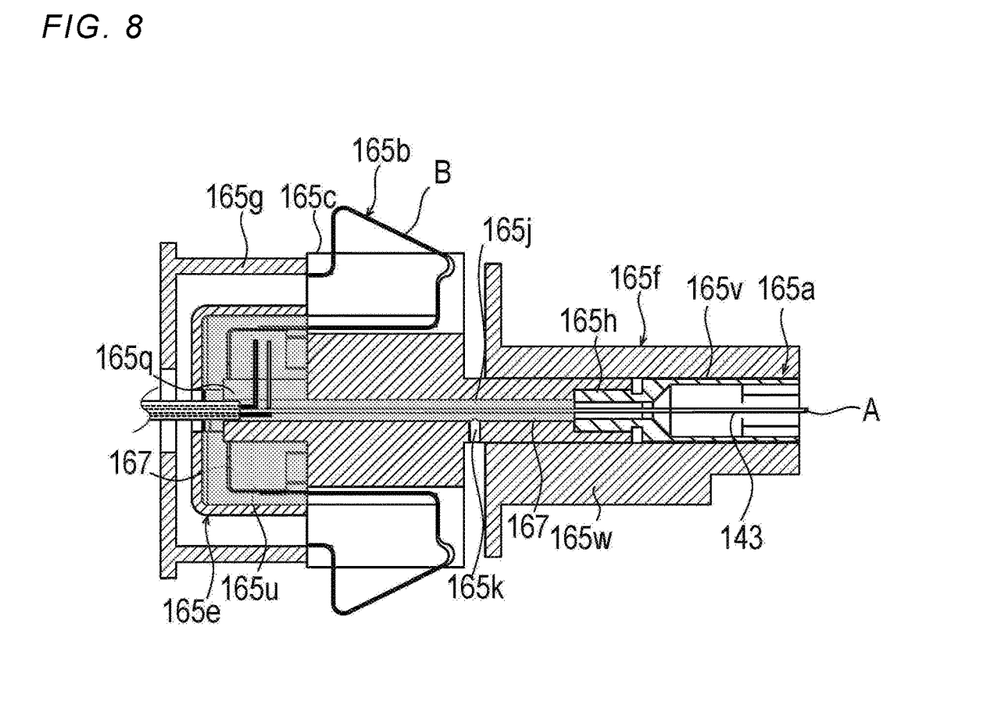
FIG. 8 is a front view of the component group as illustrated in FIG. 7.

As illustrated in FIG. 8, the connector portion 165 is provided with the optical connector 165a optically connected to the optical fiber 143, and the electrode terminal 165b (corresponding to electrical connector) electrically connected to the electric signal cable 142. As illustrated in FIGS. 6 and 7, the connector portion 165 is provided with a connector member 165c (corresponding to connection member) for disposing the electrode terminal 165b, a bracket 165d attached to the electrode terminal 165b, and a cap 165e that partially covers the connector member 165c. As illustrated in FIGS. 6 and 7, the connector portion 165 is provided with a connector cover 165f that partially covers the proximal end of the connector member 165c and covers the optical connector 165a, and a cap cover 165g that covers the cap 165e from the outside. Hereinafter, the optical connector 165a, the electrode terminal 165b, and the connector member 165c will be described.

As illustrated in FIGS. 6 and 7, the optical connector 165a is connected to the proximal portion of the connector member 165c and optically connected to the optical fiber 143. The optical connector 165a is provided with an insertion portion 165h inserted into the proximal portion of the connector member 165c. The insertion portion 165h corresponds to a first connection portion in the present specification.

Figure 9:
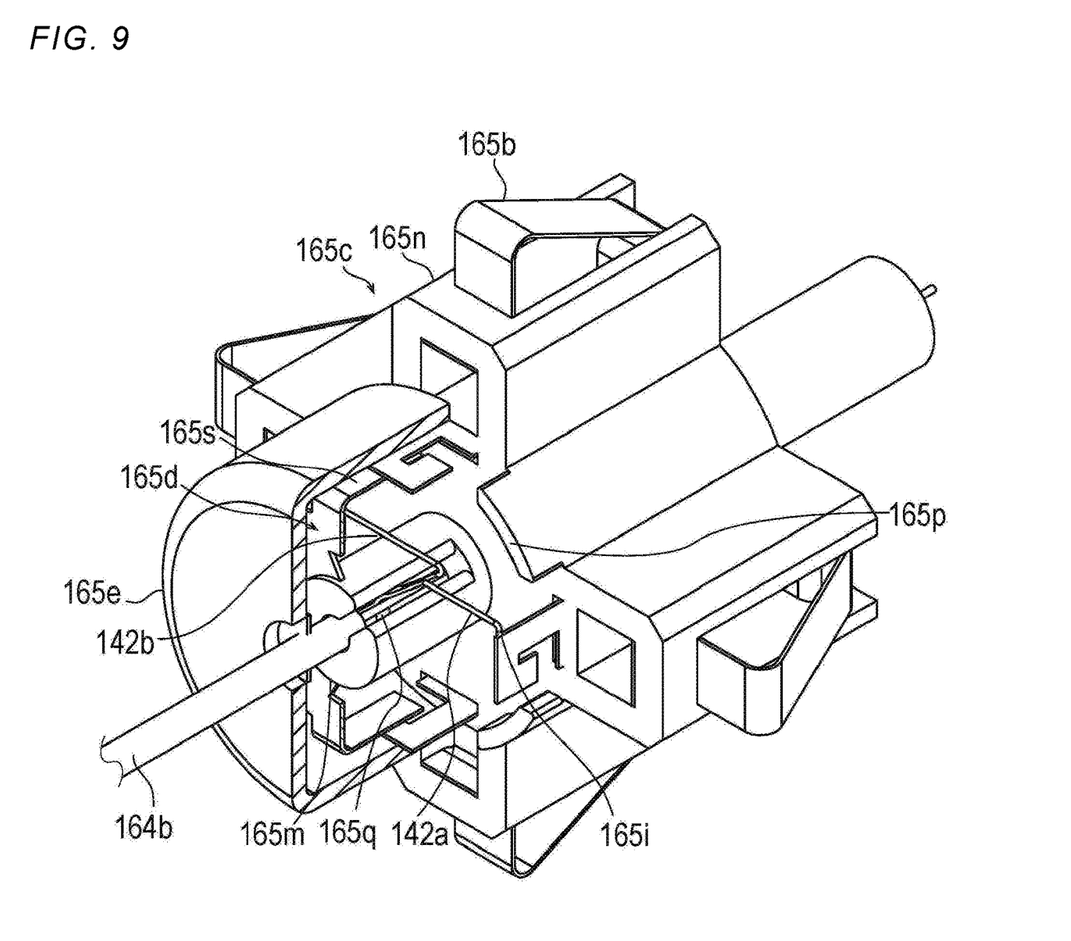
FIG. 9 is a perspective view illustrating a portion of the component group illustrated in FIG. 5 and illustrating a connection between an electric signal cable and an electrode terminal.

In accordance with an exemplary embodiment, the electrode terminal 165b can be attached, for example, to a portion provided at four (4) locations on the outer periphery of the connector member 165c. As illustrated in FIG. 9, the electrode terminal 165b is provided with a contact portion 165i attached to an attachment portion 165s of the electric signal cable 142 or the bracket 165d. In the present specification, the contact portion 165i to which the electric signal cable 142 is attached corresponds to a second connection portion, and can be disposed, for example, at intervals of 180 degrees in FIG. 9. The contact portion 165i is electrically connected to the two signal lines 142a and 142b at two of the four locations. In accordance with an exemplary embodiment, the contact portion 165i is formed in a substantially hook shape in the present embodiment. The contact portion 165*i* is joined to the proximal portion of the electric signal cable 142, for example, by solder or the like. However, the shape of the contact portion is not limited to the above as long as the electric signal cable 142 can be joined. In addition, the electrode terminal 165*b* is provided with a connection portion B electrically connected to an external electrode terminal (not illustrated) provided in the external device 300 outside in the radial direction as illustrated in FIG. 8.

The connector member 165*c* is attached with the electrode terminal 165*b* and the optical connector 165*a* on the proximal end, and is provided with a seal portion that seals each attachment portion from a portion through which the solution flows in the internal space 166*a* of the connector case 161*a*. As illustrated in FIG. 7, the connector member 165*c* is provided with an insertion part 165*j* having a cavity through which the optical fiber 143 is inserted from the distal end to the proximal end, and a communication hole 165*k* for introducing a filler 167 into the insertion part 165*j*. As illustrated in FIG. 9, the connector member 165*c* is provided with an outer wall portion 165*m* provided with a guiding portion 165*q* for guiding the electric signal cable 142 to the outside, and a mounting portion 165*n* for mounting the electrode terminal 165*b*. The connector member 165*c* is provided with an attachment portion 165*p* for attaching the cap 165*e*.

As illustrated in FIGS. 7 and 8, the insertion part 165*j* is provided inside from the distal end to the proximal end of the connector member 165*c*. The connection pipe 164*b* is disposed from the internal space 166 of the hub main body 161 to the internal space 166*a* of the connector case 161*a*, and is partially inserted at the distal end of the outer wall portion 165*m*. The optical fiber 143 is inserted into the insertion part 165*j*, and the electric signal cable 142 is partially accommodated on the distal end. While the connection pipe 164*b* and the bearing 164*c* are sealed by the sealing member 164*a*, a solution such as a priming solution can flow from the internal space 166 of the hub main body 161 to the internal space 166*a* of the connector case 161*a* in the connection pipe 164*b*. In accordance with an exemplary embodiment, in the insertion part 165*j*, the solution flowing from the distal end of the connection pipe 164*b* flows to the proximal end side, and the insertion part 165*j* is filled with the filler 167 aforementioned (gray portion in FIG. 8) from the communication hole 165*k* so that the first connection portion between the optical fiber 143 and the optical connector 165*a* does not infiltrate. In the present specification, the filler 167 constitutes a first seal portion in a state where the insertion part 165*j* is filled.

As illustrated in FIG. 8, the communication hole 165*k* can be formed, for example, by drilling the outer surface of the connector member 165*c* and extending in the radial direction or the diameter direction so as to communicate with the cavity of the insertion part 165*j*. The communication hole 165*k* is provided at a substantially central portion in the axial direction of the connector member 165*c*. In the present embodiment, the filler 167 contains a UV curable adhesive. However, the adhesive is not limited to a UV curable adhesive as long as the solution, for example, the priming solution existing on the distal end can be prevented from flowing to the proximal end, and other than the above, for example, an epoxy two-component curable adhesive or a cyanoacrylate-based adhesive may be used. The insertion part 165*j* is filled with the filler 167 through the communication hole 165*k*, and by filling more than the volume of the insertion part 165*j*, for example, the filler 167 overflows from the guiding portion 165*q*, and thereby it can be confirmed that the filler is sufficiently filled. However, the amount of the filler 167 filled in the insertion part 165*j* may not necessarily fill the entire space of the insertion part 165*j* as long as the solution can be prevented from flowing through the optical connector 165*a*.

As illustrated in FIG. 9, the outer wall portion 165*m* is provided on the distal end of the mounting portion 165*n* at the time of assemble. In the present embodiment, the outer wall portion 165*m* is formed in a substantially cylindrical shape, and as long as the electric signal cable 142 can be led out by the guiding portion 165*q*, the specific shape of the outer wall portion 165*m* is not limited to being a substantially cylindrical shape. The electric signal cable 142 and the optical fiber 143 are inserted into the tubular body 141 on the distal end, inserted into the connection pipe 164*b* on the proximal end, and the proximal end is exposed from the connection pipe 164*b*. In the present embodiment, the guiding portion 165*q* is configured to include a slit that guides the electric signal cable 142 to the contact portion 165*i* as the second connection portion. The guiding portion 165*q* is formed by cutting out one portion of the cylindrical side surface of the outer wall portion 165*m*, and the two signal lines 142*a* and 142*b* forming the electric signal cable 142 are led out to the outside from the guiding portion 165*q*. However, when the electric signal cable 142 can be led out to the outside, the specific shape and number of the guiding portions are not limited to the above.

The mounting portion 165*n* is a portion where the electrode terminal 165*b* is mounted on the connector member 165*c* as illustrated in FIG. 9. The connector member 165*c* is formed as a mounting portion 165*n* by providing a plurality of locations outward of the cylindrical shape in the radial direction, for example, in FIG. 9, four locations where the electrode terminals are mounted. The mounting portions 165*n* are provided at intervals of approximately 90 degrees in the angular direction when viewed from the front in the axial direction of the electric signal cable 142 in FIG. 9. However, the disposition of the mounting portion 165*n* is not limited to the above as long as the electrical connection between the electric signal cable 142 and the electrode terminal 165*b* can be secured.

As illustrated in FIG. 9, the attachment portion 165*p* is configured in a radial or radial inward direction with respect to the mounting portion 165*n* and has a shape like a projection protruding toward the distal end side in the assembled state. The attachment portions 165*p* can be provided at intervals, for example, of approximately 90 degrees in the angular direction or circumferential direction of the connector member 165*c* in FIG. 9. However, as long as the cap 165*e* can be attached, the number and position of the attachment portions are not limited to those as illustrated in FIG. 9.

The bracket 165*d* is a component that is attached to the connector member 165*c* via the electrode terminal 165*b*. As illustrated in FIGS. 6 and 9, the bracket 165*d* is provided with an insertion part 165*r* into which the electric signal cable 142 and the optical fiber 143 are inserted, and the attachment portion 165*s* extending from the insertion part 165*r* toward the proximal end when assembled. The insertion part 165*r* has a substantially circular outer shape, and is formed by hollowing out the inside so that the electric signal cable 142 and the optical fiber 143 can be inserted. The attachment portion 165*s* extends from two locations on the outer periphery of the insertion part 165*r* toward the proximal end side, and contacts with the contact portion 165*i* of the electrode terminal 165*b* when assembled, and is joined, for example, by soldering or the like.

As illustrated FIGS. 7 and 8, the cap 165e is attached to the distal end of the connector member 165c and covers the contact portion 165i corresponding to the second connection portion in the assembled state. The cap 165e is formed in a hollow, substantially cylindrical shape, and is provided with the connection pipe 164b, an insertion hole 165t through which the electric signal cable 142 and the optical fiber 143 are inserted, and a covering space 165u that covers a portion of the distal end of the connector member 165c and the contact portion 165i in the assembled state. The insertion hole 165t can be formed, for example, by cutting out a portion corresponding to a cylindrical bottom surface into a substantially circular shape. However, the specific shape is not limited to the above as long as the solution can be prevented from entering a sealing portion described later.

The covering space 165u corresponds to the inside of a hollow cylindrical shape. The cap 165e surrounds the outer wall portion 165m and the bracket 165d of the connector member 165c from the outside when assembled. The covering space 165u is closed by attaching the cap 165e to the connector member 165c (refer to gray translucent portion in FIG. 8). The contact portion 165i of the electrode terminal 165b is positioned in the covering space 165u of the cap 165e, and the covering space 165u is filled with the same filler 167 as that filled in the insertion part 165j. The end portion on the proximal end side of the electric signal cable 142 connected to the electrode terminal 165b is located in the covering space 165u. In accordance with an exemplary embodiment, the electric signal cable 142 can include a fluorine-based resin such as PTFE or ETFE as an outer surface material in at least a portion in the covering space 165u. As the filler 167, a UV curable adhesive or the like can be used in the same manner as aforementioned so that the attachment portion of the electric signal cable 142 and the electrode terminal 165b does not infiltrate with the solution. In addition, it can be preferable to perform surface modification processing such as tetra-etching processing or primer processing on the portion of the electric signal cable 142 located in the covering space 165u from the viewpoint of adhesiveness with the above-described adhesive. In the present specification, a second seal portion is formed by attaching the cap 165e to the connector member 165c, covering the contact portion 165i, and filling the covering space 165u including the guiding portion 165q with the filler 167.

The connector cover 165f is disposed in the internal space 166a of the connector case 161a as illustrated in FIG. 8, and can be provided with an accommodation space 165v for accommodating the proximal portion of the connector member 165c and the optical connector 165a. In addition, the connector cover 165f is provided with a keyway 165w for connecting a component (external optical connector) of the external device 300. The external optical connector (not illustrated) is connected to a right end surface A of the optical fiber 143 inserted into the optical connector 165a accommodated in the accommodation space 165v of the connector cover 165f in FIG. 8.

Figure 5:
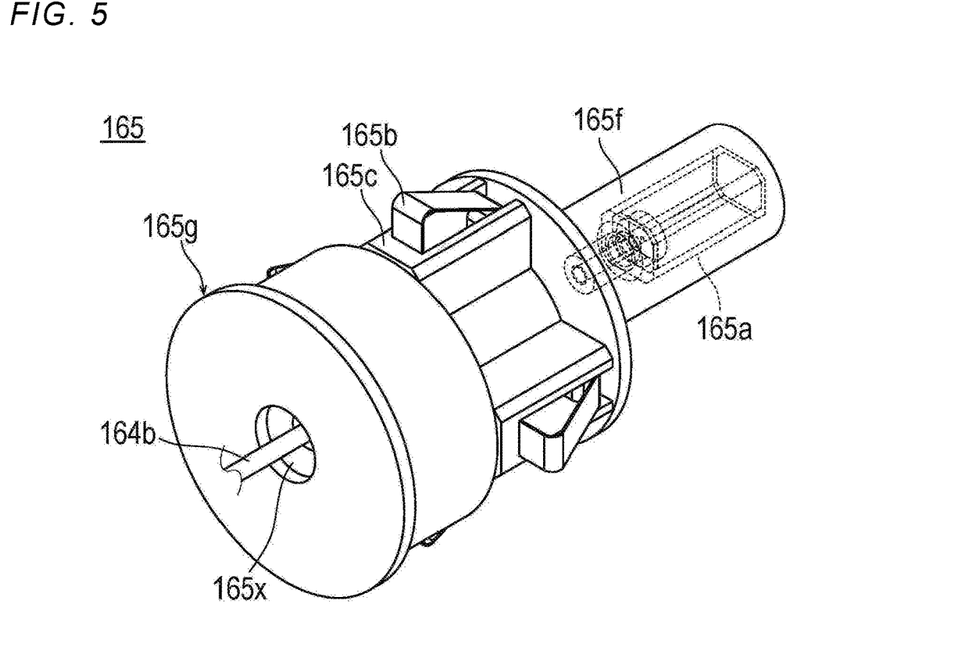
FIG. 5 is a perspective view illustrating a configuration of a connector portion illustrated in FIG. 4.

As illustrated in FIG. 4, the cap cover 165g is disposed in the internal space 166a of the connector case 161a at the time of assemble, and covers the cap 165e from the outside. As illustrated in FIG. 5, the cap cover 165g has a substantially hollow cylindrical shape like the cap 165e, and is provided with an insertion hole 165x into which the connection pipe 164b, the electric signal cable 142, and the optical fiber 143 are inserted. In addition, the cap cover 165g and the connector cover 165f can be provided with one set or a plurality of sets of arcuate wall surface shapes (i.e., curved wall surface shapes) to be attached by fitting as an example in the angular direction so that both are mechanically connected. However, the specific shape is not limited to the above as long as both can be mechanically connected.

Next, an example of use in a case where the diagnostic imaging catheter 100 is inserted into a blood vessel 900, which is an example of a biological lumen, will be described.

First, the user connects the injection device S for injecting the priming solution to the port 162 with the hub 160 pulled to the most proximal end (refer to FIG. 2B), and pushes a plunger of the first syringe S4 to inject the priming solution into the lumen 110a of the sheath 110. Note that, in a case where the amount of the priming solution injected by the first syringe S4 is insufficient, the priming solution is injected into the lumen 110a of the sheath 110 by pushing a plunger of the second syringe S5.

When the priming solution is injected into the lumen 110a, the priming solution is discharged to the outside of the sheath 110 through the communication passage 117a and the communication hole 116 illustrated in FIG. 3. As a result, a gas such as air can be discharged from the inside of the sheath 110 to the outside together with the priming solution (priming processing).

After the priming processing, the user connects the external device 300 to the connector portion 165 of the diagnostic imaging catheter 100 as illustrated in FIG. 1. The user pushes the hub 160 until the hub 160 attaches the proximal end of the unit connector 150 (refer to FIG. 2A), and moves the signal transmitter and receiver 145 to the distal end side.

Next, the user creates a port on the wrist or thigh using an introducer kit. Next, a first guide wire (not illustrated) is inserted through the port to the vicinity of a coronary artery entrance of the heart. Next, a guiding catheter 800 is introduced to the coronary artery entrance through the first guide wire. Next, the first guide wire is removed, and a second guide wire W is inserted into a lesion area through the guiding catheter 800. Next, the diagnostic imaging catheter 100 is inserted into the lesion area along the second guide wire W.

Figure 10A:
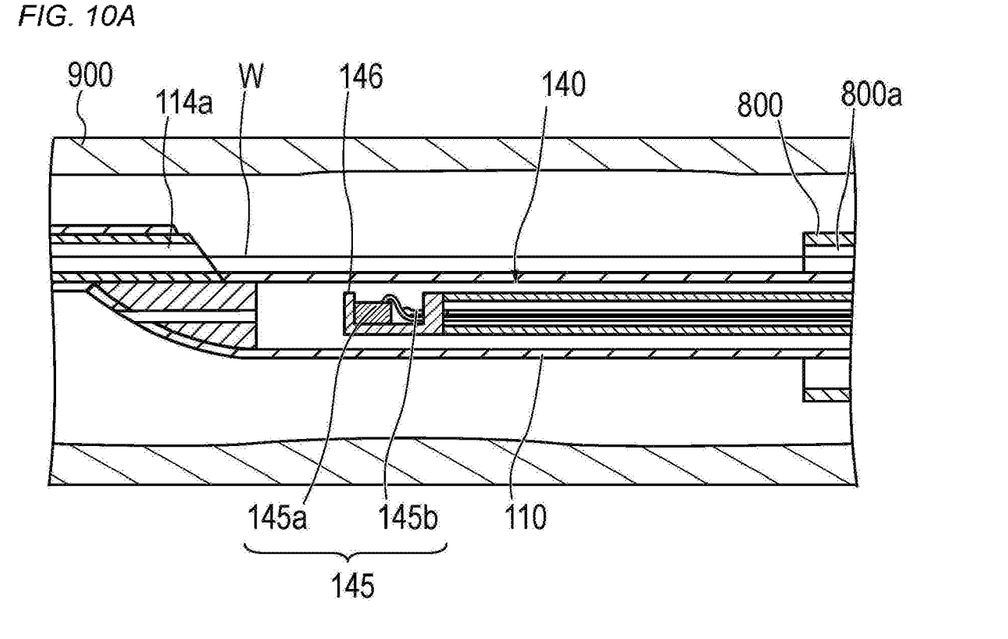
FIGS. 10A and 10B are schematic views illustrating an example of use of the diagnostic imaging catheter according to the embodiment.

Next, as illustrated in FIG. 10A, the diagnostic imaging catheter 100 is advanced along the lumen 800a and protruded from a distal opening portion of the guiding catheter 800. Thereafter, while the second guide wire W is inserted through the guide wire lumen 114a, the diagnostic imaging catheter 100 is further pushed along the second guide wire W to be inserted into a target position in the blood vessel 900. Note that, as the guiding catheter 800, a known guiding catheter provided with a port (not illustrated) to which a syringe (not illustrated) can be connected at a proximal portion can be used.

Next, the blood in the blood vessel 900 is temporarily replaced with a flush solution such as a contrast agent. Similarly to the priming processing aforementioned, the syringe containing the flush solution is connected to the port of the guiding catheter 800, and the plunger of the syringe is pushed to inject the flush solution into the lumen 800a of the guiding catheter 800. As illustrated by an arrow C in FIG. 10B, the flush solution passes through the lumen 800a of the guiding catheter 800 and is introduced into the blood vessel 900 through the distal opening portion. The blood around the distal portion of the sheath 110 is washed away by the introduced flush solution, and the flush solution is filled around the distal portion of the sheath 110. Note that, in the mode of acquiring a tomographic image only by IVUS, the above-described step of replacing with the flash solution can be omitted.

Figure 10B:
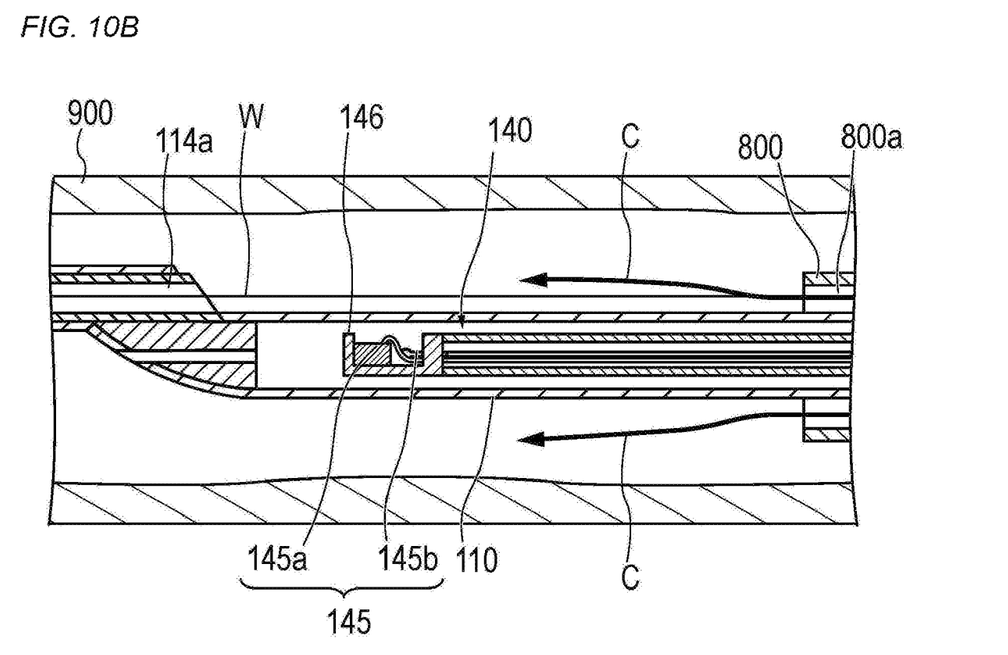

When obtaining a tomographic image at a target position in the blood vessel 900, the signal transmitter and receiver 145 moves to the proximal end side while rotating with the drive shaft 140 (pull-back operation). Simultaneously with the pull-back operation, as illustrated in FIGS. 10A and 10B, the ultrasound transmitter and receiver 145a transmits the ultrasound toward a blood vessel wall 900b and receives the ultrasound reflected by the blood vessel wall 900b. In addition, the optical transmitter and receiver 145b simultaneously transmits the measurement light toward the blood vessel wall 900b and receives the reflected light reflected by the blood vessel wall 900b. Note that, as aforementioned, since the ultrasound transmitted from the ultrasound transmitter and receiver 145a intersects with the measurement light transmitted from the optical transmitter and receiver 145b, a region to be inspected by the ultrasound in the living body and a regions to be inspected light can be overlapped.

Note that the rotation and movement operation of the drive shaft 140 is controlled by the control apparatus 301. The connector portion 165 provided in the hub 160 is rotated while being connected to the external device 300, and the drive shaft 140 is rotated in conjunction with the rotation.

In addition, the signal transmitter and receiver 145 transmits the ultrasound and light into the body based on the signal sent from the control apparatus 301. A signal corresponding to the reflected wave and the reflected light received by the signal transmitter and receiver 145 is sent to the control apparatus 301 via the drive shaft 140 and the external device 300. The control apparatus 301 generates a tomographic image of the biological lumen based on the signal sent from the signal transmitter and receiver 145 and displays the generated image on the monitor 330.

Hereinbefore, the diagnostic imaging catheter 100 according to the present embodiment is provided with the rotatable drive shaft 140 in which the optical transmitter and receiver 145b and the ultrasound transmitter and receiver 145a are disposed on the distal portion, and the optical fiber 143 connected to the optical transmitter and receiver 145b and the electric signal cable 142 connected to the ultrasound transmitter and receiver 145a are disposed, the elongated sheath 110 is configured to be inserted into the biological lumen, into which the drive shaft 140 can be inserted, and the elongated sheath including the lumen 110a through which the solution flows, the hub 160 that includes the port 162 connected to the sheath 110 for supplying the solution, and the internal space 166 communicating with the lumen 110a of the sheath 110, through which the solution flows, and the optical fiber 143 and the electric signal cable 142 are inserted, the connector portion 165 can include the optical connector 165a accommodated in the internal space 166a of the hub 160 and optically connected to the external optical connector provided in the external device 300 and the optical fiber 143, and the electrode terminal 165b electrically connected to the external electrode terminal provided in the external device 300 and the electric signal cable 142, the first seal portion that helps prevents the solution from the port 162 from flowing into the first connection portion between the optical connector 165a and the optical fiber, and the second seal portion that helps prevents the solution from the port 162 from flowing into the second connection portion between the electric signal cable 142 and the electrode terminal 165b.

Therefore, the first connection portion between the optical connector 165a and the optical fiber 143 is sealed by the first seal portion. In addition, the second connection portion between the electrode terminal 165b and the electric signal cable 142 is sealed by the second seal portion. Therefore, the solution from the internal space 166 of the hub 160 can be prevented from flowing into a portion communicating with the internal space 166 of the hub 160 and to which the signal lines such as the optical fiber 143 and the electric signal cable 142 are electrically or optically connected.

In addition, the connector portion 165 is provided with the connector member 165c to which the optical connector 165a is attached. The connector member 165c is provided with the insertion part 165j provided with the cavity into which the optical fiber 143 is inserted from the distal end to the proximal end, and the first seal portion includes the filler 167 filled in the cavity of the insertion part 165j. Therefore, by filling the cavity with the filler 167, it is possible to help prevent the solution from flowing into the insertion part 165j and to help prevent the solution from flowing into the first connection portion.

In addition, the connector member 165c can include the communication hole 165k that communicates from the outer surface to the cavity of the insertion part 165j. Therefore, when the diagnostic imaging catheter 100 is assembled, the filler 167 can be filled into the insertion part 165j of the connector member 165c from the communication hole 165k to help prevent the solution from flowing into the first connection portion.

In addition, the electric signal cable 142 is partially accommodated in the insertion part 165j of the connector member 165c. The connector member 165c is provided with the guiding portion 165q for guiding the electric signal cable 142 accommodated in the insertion part 165j to the second connection portion, and the mounting portion 165n for mounting the electrode terminal 165b. The connector portion 165 is provided with the cap 165e attached to the connector member 165c and covers the second connection portion in a state assembled to the connector member 165c. The second seal portion is formed by attaching the cap 165e to the connector member 165c to cover the second connection portion and filling the covering space 165u with the filler 167. Therefore, the solution can be prevented from flowing into the second connection portion between the electrode terminal 165b and the electric signal cable 142 by the cap 165e and the filler 167 filled in the covering space 165u.

In addition, the filler 167 includes an adhesive, the electric signal cable 142 includes a fluorine-based resin on the surface, and the surface of the electric signal cable 142 is configured to be subjected to surface processing that provides adhesiveness such as tetra-etching processing or primer processing. Therefore, when the covering space 165u of the cap 165e is filled with the adhesive as the filler 167, the electric signal cable 142 can be prevented from being unintentionally displaced in the covering space 165u of the cap 165e by imparting adhesiveness to the electric signal cable 142. In other words, the adhesion between the adhesive and the electric signal cable 142 can be prevented from being separated. Therefore, it can contribute to help prevent the solution from entering to the second connection portion.

Note that the present disclosure is not limited to the above-described embodiment, and various modifications can be made within the scope of the aspects. In the above description, it has been described that the two electric signal cables 142 illustrated in FIG. 9 are disposed, for example, at intervals of 180 degrees when viewed from the front with the axial direction of the drive shaft 140 as the front. However, the disclosure is not limited to the two electric signal cables 142 being at intervals of 180 degrees, and for example, two electric signal cables may be connected to the electrode terminal 165b at intervals of 90 degrees or 270 degrees as long as these can be connected to any electrode terminal.

In addition, the embodiment has been described in which the outer wall portion 165m is provided on the distal end with respect to the mounting portion 165n to which the electrode terminal 165b is attached in the assembled state. However, the invention is not limited to the outer wall portion 165m being provided on the distal end with respect to the mounting portion 165n to which the electrode terminal 165b is attached. In addition to the above, the outer wall portion 165m may be formed so as to protrude to the proximal end with respect to the mounting portion 165n in the assembled state.

In addition, the hub 160 has been described as including the hub main body 161 and the connector case 161a as the casing, and the invention is not limited to the hub 160 including the hub main body 161 and the connector case 161a as the casing. For example, the hub main body 161 and the connector case 161a may be configured as one component.

In addition, in the above description, the embodiment has been described in which the diagnostic imaging catheter according to the present disclosure is applied to an diagnostic imaging catheter having the functions of the intra vascular ultra sound (IVUS) diagnosis method and the optical coherence tomography (OCT) diagnosis method. The diagnostic imaging catheter according to the present disclosure is not particularly limited as long as the diagnostic imaging catheter uses the ultrasound and light as inspection waves. Therefore, in addition to the above, for example, the disclosure may be applied to a diagnostic imaging catheter having functions of IVUS and an optical frequency domain imaging (OFDI) method.

For example, in the above embodiment, the embodiment has been described in which the electric signal cable (signal line) is configured to include two cables extending like parallel lines (i.e., the two cables are parallel to one another). The electric signal cable may be configured to include, for example, a coaxial cable (one cable). In addition, the electric signal cable may be configured to include a twisted pair cable in which two cables are wound around an optical fiber.

The detailed description above describes embodiments of a diagnostic imaging catheter. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A diagnostic imaging catheter comprising:
a rotatable drive shaft having an optical transmitter and receiver and an ultrasound transmitter and receiver disposed on a distal portion of the rotatable drive shaft, and an optical fiber connected to the optical transmitter and receiver and a signal line connected to the ultrasound transmitter and receiver;
an elongated sheath configured to be inserted into a biological lumen, the drive shaft configured to be inserted into the elongated sheath, and the elongated sheath including a lumen through which a solution flows;
a hub that includes a port supplying the solution to the lumen of the sheath, and an internal space communicating with the lumen of the sheath, the lumen configured to receive the solution from the port and wherein the optical fiber and the signal line are inserted into the lumen;
a connector portion that includes an optical connector accommodated in the internal space of the hub and optically connected to an external optical connector provided in an external device and the optical fiber, and an electrical connector electrically connected to an external electrical connector provided in the external device and the signal line;
a first seal portion configured to prevent the solution from the port from flowing into a first connection portion between the optical connector and the optical fiber;
a second seal portion configured to prevent the solution from the port from flowing into a second connection portion between the signal line and the electrical connector; and
the connector portion further includes a connection member attaching the optical connector, the connection member includes an insertion part having a cavity through which the optical fiber is inserted from a distal end to a proximal end, and wherein the first seal includes a filler within the cavity of the insertion part, the filler within the cavity of the insertion part configured to prevent the solution from flowing through the insertion part.

2. The diagnostic imaging catheter according to claim 1, wherein the connection member includes a communication hole communicating with the cavity of the insertion part from an outer surface.

3. The diagnostic imaging catheter according to claim 1, wherein the signal line is partially accommodated in the insertion part, and the connection member includes a guiding portion guiding the signal line accommodated in the insertion part to the second connection portion, and a mounting portion mounting the electrical connector.

4. The diagnostic imaging catheter according to claim 3, wherein the connector portion includes a covering member that is attached to the connection member and that forms a covering space covering the second connection portion in a state attached to the connection member, and the second seal portion is formed by assembling the covering member to the connection member to cover the second connection portion and filling the covering space with a filler.

5. The diagnostic imaging catheter according to claim 4, wherein the filler of the covering space includes an adhesive.

6. The diagnostic imaging catheter according to claim 5, wherein the adhesive of the covering space is a UV curable adhesive.

7. The diagnostic imaging catheter according to claim 5, wherein the signal line contains a fluorine-based resin on a surface, and the surface of the signal line is subjected to a surface processing which improves an adhesive force to the adhesive.

8. The diagnostic imaging catheter according to claim 1, wherein the filler within the cavity of the insertion part includes an adhesive.

9. The diagnostic imaging catheter according to claim 8, wherein the adhesive within the cavity of the insertion part is a UV curable adhesive.

10. A connector for a diagnostic imaging catheter, the connector comprising:
a connector portion that includes an optical connector accommodated in the internal space of a hub configured to supply a solution to a lumen of an elongated sheath, the lumen being optically connected to an external optical connector provided in an external device and an optical fiber connected to an optical transmitter and receiver, and an electrical connector electrically connected to an external electrical connector provided in the external device and a signal line connected to an ultrasound transmitter and receiver;

a first seal portion configured to prevent the solution from a port from flowing into a first connection portion between the optical connector and the optical fiber;

a second seal portion configured to prevent the solution from the port from flowing into a second connection portion between the signal line and the electrical connector; and the connector portion further includes a connection member attaching the optical connector, the connection member includes an insertion part having a cavity through which the optical fiber is inserted from a distal end to a proximal end, and wherein the first seal includes a filler within the cavity of the insertion part, the filler within the cavity of the insertion part configured to prevent the solution from flowing through the insertion part.

11. The connector according to claim 10, wherein the connection member includes a communication hole communicating with the cavity of the insertion part from an outer surface.

12. The connector according to claim 10, wherein the signal line is partially accommodated in the insertion part, and the connection member includes a guiding portion guiding the signal line accommodated in the insertion part to the second connection portion, and a mounting portion mounting the electrical connector.

13. The connector according to claim 12, wherein the connector portion includes a covering member that is attached to the connection member and that forms a covering space covering the second connection portion in a state attached to the connection member, and the second seal portion is formed by assembling the covering member to the connection member to cover the second connection portion and filling the covering space with a filler.

14. The connector according to claim 13, wherein the filler of the covering space includes an adhesive.

15. The connector according to claim 14, wherein the adhesive of the covering space is a UV curable adhesive.

16. The connector according to claim 14, wherein the signal line contains a fluorine-based resin on a surface, and the surface of the signal line is subjected to a surface processing which improves an adhesive force to the adhesive.

17. The connector according to claim 10, wherein the filler within the cavity of the insertion part includes an adhesive.

18. The connector according to claim 17, wherein the adhesive within the cavity of the insertion part is a UV curable adhesive.

19. A method for using a diagnostic imaging catheter, the method comprising:

injecting a solution into a lumen of an elongated sheath of the diagnostic imaging catheter through a connector portion that includes an optical connector accommodated in an internal space of a hub configured to supply the solution to the lumen of an elongated sheath and optically connected to an external optical connector provided in an external device and an optical fiber connected to an optical transmitter and receiver and, and an electrical connector electrically connected to an external electrical connector provided in the external device and a signal line connected to an ultrasound transmitter and receiver, the connector portion including a connection member attaching the optical connector, and the connection member includes an insertion part having a cavity through which the optical fiber is inserted from a distal end to a proximal end;

preventing the solution from a port from flowing into a first connection portion between the optical connector and the optical fiber with a first seal portion, the first seal including a filler within the cavity of the insertion part; and preventing the solution from the port from flowing into a second connection portion between the signal line and the electrical connector with a second seal portion.

20. The method according to claim 19, further comprising:

forming the second seal portion by assembling a covering member to the connection member to cover the second connection portion that forms a covering space covering the second connection portion in a state attached to the connection member; and filling the covering space with the same filler as the first connection portion.

* * * * *